United States Patent [19]

Gelfand et al.

[11] Patent Number: 4,870,013

[45] Date of Patent: Sep. 26, 1989

[54] SV40 EARLY AND RSV PROMOTERS USEFUL IN SACCHAROMYCES EXPRESSION

[75] Inventors: David H. Gelfand; Frances C. Lawyer, both of Oakland; Susanne Stoffel, El Cerrito, all of Calif.

[73] Assignee: Cetus Corporation, Emeryville, Calif.

[21] Appl. No.: 196,789

[22] Filed: May 18, 1988

Related U.S. Application Data

[63] Continuation of Ser. No. 618,960, Jun. 11, 1984, abandoned, which is a continuation-in-part of Ser. No. 602,118, Apr. 19, 1984, Pat. No. 4,784,949.

[51] Int. Cl.$^4$ .................... C12P 21/00; C12N 15/00; C12N 5/00
[52] U.S. Cl. .................................. 435/68; 435/172.3; 435/91; 435/323; 435/255; 435/256; 935/27; 935/28; 935/29; 935/37
[58] Field of Search ............... 435/68, 70, 91, 172.3, 435/255, 256, 235, 253, 240.2, 320, 948; 935/27, 28, 29, 32, 36, 37, 39, 41, 56, 70, 69, 73, 72

[56] References Cited

U.S. PATENT DOCUMENTS 4,510,245  4/1985  Cousens et al. ................ 435/172.3

FOREIGN PATENT DOCUMENTS 2100738  1/1983  United Kingdom ................ 435/317

OTHER PUBLICATIONS

Granovskii et al., *Chem. Abst.*, vol. 100, No. 151949q, 1984, "Cloning and Expression of SV40 Genome in *Succharomyces Cerevisiae* Cells".
Granovskii et al., *Chem. Abst.*, vol. 99, No. 33877p, 1983, "Cloning of the SV40 Genome with the Yeast Vector YEp13".
Auezova et al., *Chem. Abst.*, vol. 103, No. 208037v, 1985, "Transcription of the SV40 Genome in the Yeast *Succharomyces Cerevisiae*".
Arman et al., *Chem. Abst.*, vol. 102, No. 107442x, 1985, "Replication of Hybrid Plasmids Containing the Complete Genome of Supins".
Henikoff et al., 1981, "Isolation of a Gene from *Drosophila* by Complementation in Yeast" (Abstract) *Nature*, v. 289, pp. 33-37.
Beggs et al., 1980, "Abnormal Expression of Chromosomal Rabbit B-Globin Gene in Saccharomyces Cerevisiae" *Nature* (Abstract) v. 283, pp. 835-840.
Gormun, et al., *Proc. Natl. Acad. Sci.*, vol. 79, pp. 6777-6781, 1982, "The Rous Sarcoma Virus Long Terminal Repeat is a Strong Promotor When Introduced into a Variety of Eukaryotic Cells by DNA-Mediated Transfection".
Mercereau-Puijalon et al., *Chem. Abst.*, vol. 94, No. 27229j, 1981, "Synthesis of a Chicken Ovalbumin-Like Protein in the Yeast *Saccharomyces Cerevisiae*".
Yamamoto et al., *Mol Gen Genet* 1981, vol. 182, pp. 426-429, "Cloning of a Gene from the Fission Yeast *S. Pambe* which Compliments *E. coli* pyrB, the Gene for Aspartate Transcarbamylase".

*Primary Examiner*—Robin Teskin
*Attorney, Agent, or Firm*—Kate H. Murashige; Lisabeth F. Murphy; Albert P. Halluin

[57] ABSTRACT

Expression vectors containing coding sequences under the control of SV40 early and RSV promoters are disclosed as useful in producing proteins in saccharomyces yeasts. Construction of such vectors, and their use in yeast transformations are described.

8 Claims, 7 Drawing Sheets

| Plasmid | DNA Sequence & Deduced Amino Acid Sequence | MIC – 50% |
|---|---|---|
| pNG56 | 1 10 11 12 13 14 15 16 17 18 19 20<br>Met...Cys Ser Arg Pro Arg Leu Asn Ser Asn Met Asp<br>AAGGGGTGTT ATG...TGC TCG AGG CCG CGA TTA AAT TCC AAC ATG GAT | >300µg/ml |
| MCK 4.1 | 1 2 3 4<br>Met Ser Arg Pro...<br>AAGCTT ATG TCG AGG CCG... | >300µg/ml |

SV40 EARLY AND RSV PROMOTERS USEFUL IN SACCHAROMYCES EXPRESSION

This is a file wrapper continuation of U.S. patent application Ser. No. 618,960, filed June 11, 1984, and now abandoned, which is a continuation-in-part of U.S Ser. No. 602,118, filed Apr. 19, 1984 and now U.S. Pat. No. 4,784,949.

TECHNICAL FIELD

The present invention relates to aspects of recombinant DNA technology concerned with providing suitable control sequences to effect expression in yeast hosts. More particularly, the invention relates to use of mammalian promoters to produce desired peptides in yeast.

BACKGROUND ART

A fundamental rule of molecular biology, with few exceptions, is the universality of the genetic code. While certain among degenerate codons may be favored by one type of organism or another, the same sequence of codons most usually produces the same sequence of amino acids regardless of whether the cell effecting expression is an *E. coli*, a yeast, or a cell derived from a human being or a petunia. Such versatility is not extended to the control sequences which effect the expression of the coding portions of the DNA. Promoters which are operable in bacteria do not, as a general rule, operate in eucaryotic hosts. There are, of course, some exceptions related to promoters associated with virulence of certain bacteria to their targeted host organisms. There are also other fortuitous exceptions wherein bacterial promoters operate, though more poorly, in yeast. Similarly, control sequences which are normally utilized by mammalian cells do not operate in unicellular eucaryotic hosts such as yeast or in procaryotes such as bacteria. Thus, the standard approach to securing the production of desired peptide in a particular host is to ligate the coding sequence for the desired peptide in suitable juxtaposition to control sequences indigenous to the host used to produce the protein.

In eucaryotic sytems, at least two and in some cases three, elements of control sequences are considered relevant to successful expression: a sequence 5' of the start codon which is responsible for the initiation of transcription (the promoter) and a sequence 3' of the. cdding sequence which appears to contain at least a polyadenylation signal which apparently is instrumental in transporting the RNA transcript from the nucleus to the cytoplasm (the terminator). Thus, to secure expression in a eucaryote, it has been necessary to provide indigenous promoters and terminators in operable linkage to the desired coding sequence.

In addition, it has recently been shown that "enhancers" of expression may be involved in protein production for certain specialized mammalian cells. Enhancers of viral origin which can operate in eucaryotic hosts have been known for some time. These enhancer sequences are apparently relatively insensitive to orientation and position, and function to increase expression levels of associated expression packages.

Yeast hosts have been successfully transformed and induced to produce protein sequences using a variety of yeast origin vectors containing yeast promoters and terminators. See, for example, Broach, J. R., *Meth. Enz* (1983) 101:307; Stinchcomb, et al, *Nature* (1979) 282: 39, Tschempe, et al, *Gene* (1980) 10:157 and Clark, L., et al, *Meth. Enz* (1983) 101:300, Holland, M. J., et al, *J Biol Chem* (1981) 256:1385. The variety of control sequences available is quite large, and includes promoters for the synthesis of the glycolytic enzymes, for alcohol dehydrogenase, acid phosphatase, and a variety of others.

Because yeast are capable of rapid and luxuriant growth under aerobic conditions, they are ideal candidates for large scale production of proteins. Also, by altering their complement of enzymic catalysts, they may be employed to carry out chemical transformations such as hydroxylation, oxidation, isomerization, hydrolysis or utilization of targeted chemicals. Accordingly, the provision of suitable control sequences in yeast hosts provides a useful method of employing these organisms for the production of proteins and other materials. It has, heretofore, been necessary to employ control sequences of yeast origin in order to do this.

Known yeast control sequences can provide useful results; however, they have certain associated drawbacks. Since they are essentially endogenous, efforts to control heterologous protein production through control of the operably linked control sequences may have the side effect of causing undesired fluctuations in expression of the analogous endogenous system. Also, sequence identity with native controls may result in unwanted recombination into the host DNA. Finally, expression vectors intended for other species hosts, e.g., mammalian cells, which are more difficult to culture than yeast, cannot use yeast as a convenient cloning and expression manipulation host.

(In connection with the last-mentioned problem, it should be noted that versatility with respect to host, if extended to procaryotes as well, would constitute an even greater advantage for an expression control system. Control sequences which are operable in bacteria, yeast and mammalian cells offer, for example, the opportunity to study expression under a wide range of post translational processing conditions.)

In short, the necessity to use yeast control sequences carries an intrinsic limitation to the characteristics to these particular control sequences. To provide greater flexibility and control of expression in yeast, it would be desirable to add xenogeneic control sequences to the available repetoire. The present invention provides for such an increase in versatility.

DISCLOSURE OF THE INVENTION

It has been found that mammalian promoters, in particular those associated with viruses infecting mammalian hosts, are effective in yeast host expression. It is possible to include both a mammalian viral promoter and a yeast terminator sequence, but it appears that merely the promoter sequence will suffice. This results in more efficient construction of expression vectors, and provide powerful promoter systems previously unavailable for use in yeast mediated protein production. In addition, trifunctional promoter sequences operable in procaryotes, yeast, and mammalian cells provide increased versatility.

Thus, in one aspect, the invention relates to vectors effective in expressing a coding sequence for a desired protein in yeast which comprises the coding sequence operably linked to a promoter normally operable in mammalian cells. In other aspects, the invention relates to yeast cells transformed with such vectors, and to methods for producing a desired protein by culturing such cells. In still other aspects, the invention relates to expression vectors containing expression systems which include trifunctional promoters, to cells transformed with these vectors, and to methods of effecting expression with these vectors.

BRIEF DESCRIPTION OF THE DRAWINGS

FIG. 5 shows the construction of pDG144.

MODES FOR CARRYING OUT THE INVENTION

A. Definitions

Figure 1:
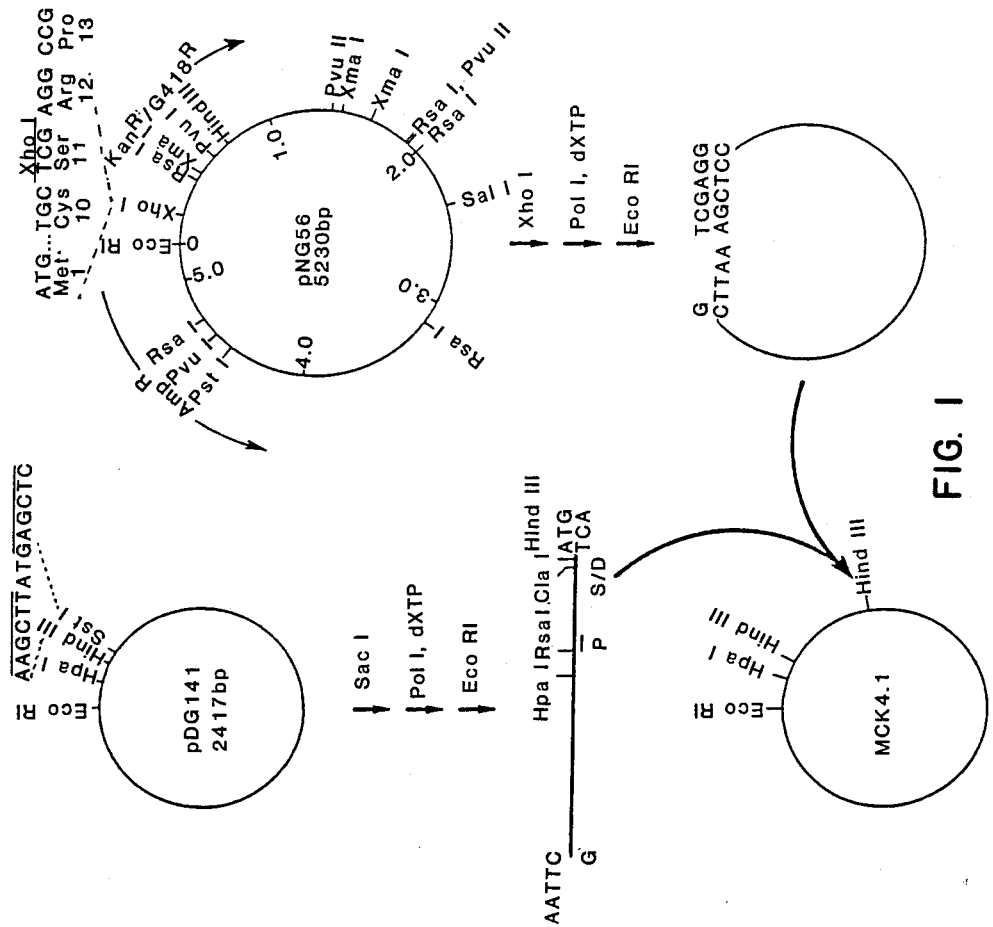
FIG. 1 shows the construction of pMCK4.1.

"Operably linked" refers to constructions wherein the components so described are juxtaposed in such a way as to permit them to function in their intended manner vis-a-vis each other. Thus, a promoter operably linked to a coding sequence refers to a promoter which is capable of effecting the transcription of the desired coding sequence "Control sequences" refers to whatever is required to effect the expression of a coding sequence in connection with a particular host. It appears that eucaryotic cells generally require, in addition to promoter sequences 5' of the coding portion of the DNA, a polyadenylation signal to assure that the messenger RNA transcribed from the gene sequences is transported out of the nucleus and translated. The nature of this process is not well understood, but it is known that certain terminator sequences which include polyadenylation signals are often necessary for effective production of desired proteins in eucaryotic hosts. Terminator sequences include the 3' untranslated region from the ENO1 gene of yeast and the nopaline synthase sequences obtainable from Agrobacterium plasmids normally operable in a plant cell hosts.

"Terminator" is intended to include whatever is required in such sequences, not necessarily limited to the polyadenylation function. This definition is necessitated by the current state of knowledge in the art, wherein the relevance of sequences in addition to the polyadenylation signal is unclear.

"Normally operable" in a particular host refers to control sequences which in their native state are expected to perform in the host in question. Thus, control sequences "normally operable" in yeast include those of yeast origin. Those "normally operable" in mammalian cells include those found natively therein and also those which function in such hosts by virtue of infection by, for example, a virus. Thus, the early and late promoters of SV40 (Simian virus 40) and those of Rous Sarcoma Virus (RSV) are considered promoters "normally operable" in mammalian cells though they themselves are viral promoters. Similarly, the crown gall producing bacterium *Agrobacterium tumefaciens* contains plasmids bearing promoters which normally function in infected plant cells. These would be "normally operable" in plants.

"Trifunctional" promoter refers to a promoter which is effective in expressing a coding sequence in all three (bacterial, yeast and mammalian) types of hosts.

"Expression system" refers to DNA sequences encoding a desired peptide in operable linkage with control sequences.

B. GENERAL DESCRIPTION

B.1. Expression in Yeast

The utility of mammalian derived promoters in effecting the production of a desired protein in transformed yeast hosts is illustrated below with respect to a dominant selectable marker protein which is capable of conferring resistance to the aminoglycoside antibiotic G418. This type of antibiotic resistance is singularly useful, because G418 is toxic not only to bacteria, but to cells in general, including yeast, plants, and mammalian cells. A detailed description of the preparation of the coding sequences for a modified truncated form of aminoglycoside phosphotransferase-I (mtAPH-I), the enzyme which is responsible for conferring this resistance is set forth in copending application, U.S. Ser. No. 602,118, now U.S. Pat. No. 4,784,949, "A Universal Dominant Selectable Marker Cassette" filed Apr. 19, 1984, assigned to the same assignee, and incorporated herein by reference. However, it will be immediately apparent, the invention is not limited to this particular coding sequence. Indeed, the coding sequence for any desired protein such as that for any of the interferons, such as leukocyte, fibroblast, and gamma-interferon, growth factors such as nerve growth factor, toxins such as diptheria toxin, growth hormones such as human growth hormone or bovine growth hormone, lymphokines such as interleukin 2, or lymphotoxin, can be used. To obtain alternate vectors for the expression of such sequences, standard techniques of recombinant technology such as those illustrated below in the construction of the disclosed vectors may be employed using alternate coding sequences. Similarly, operable mammalian promoters such as those derived from polyoma, adenovirus 2, or bovine papilloma virus may also be used.

Alternatively, the vectors illustrated below may be modified by cleavage using suitable restriction enzymes, and ligation of the fragments with the desired alternate sequences.

The two vectors illustrated below, pDG148 and pDG151::RSV are particularly appropriate to demonstrate the use of mammalian promoters in yeast systems as they provide an easy assay for successful transformation and expression. In each case, a dominant selectable marker is used as the model for the desired protein; and the coding sequence is bounded by convenient restriction sites to permit its easy excision and substitution of a desired sequence. Similarly, the SV40 and RSV promoters used to illustrate the invention are also bound by convenient restriction sites, and alternate mammalian promoters can easily be substituted. No terminator sequences 3' of the coding sequence appears necessary, though its presence may be helpful; pDG151::RSV contains such sequences, pDG148 does not.

B.2. Trifunctional Promoter

Increased versatility is obtainable if expression systems are operable in a wide range of hosts. An important result of such operability is the capacity to study post-translational processing of protein.

It has been found that the RSV promoter sequences are functional in procaryotes, yeast and mammalian cells, and that this promoter thus illustrates promoter sequences which are trifunctional. Such trifunctional promoters may be of mammalian, yeast, or bacterial origin, and can be operably linked to a desired coding sequence, for example, that for an interferon, a lymphokine, a hormone, an enzyme or other desired peptide and used to effect its expression in the aforesaid variety of hosts.

By the capability to effect this expression, the desired sequence and its expression system can be cloned and validated in the most convenient host, regardless of the ultimate cell type which will produce the desired protein. This ability is especially important where active protein requires post-translational processing, such as glycosylation, which can be performed only by a given host type, which host may be difficult to culture under convenient conditions. In that case, manipulations related to production of the amio acid sequence, independent of its subsequent processing can be performed and assessed using a host which is more convenient, and where the results of studies on protein production are not complicated by post-translational processes.

C. General Methods

Both cloning and expression vectors for desired sequences were constructed using the below described commonly employed restriction and ligation procedures. Additional plasmids, analogous to those illustrated, can also be constructed using these methods, which are well known in the art, by utilizing alternative replicons, vector fragments, control sequences, coding sequences, polylinkers, and expression cassettes.

In general, the quantity of DNA available can be increased by cloning the desired fragments, i.e., inserting into a suitable cloning vehicle, such as pBR322, transforming and replicating in *E. coli,* and, optionally, further enhancing through chloramphenicol amplification or by phage replication. For expression, the desired fragments can then be removed from the cloning vectors or phage and ligated to suitable control sequences compatible with the host intended to be employed in the expression of the gene. Such hosts are then transformed with these expression vectors and cultured under conditions which favor stabilization of the plasmid and the safe production of a desired protein.

C.1. Transformations

Transformations into yeast were carried out according to the method of Van Solingen, P., et al *J Bact* (1977) 130:946 and Hsiao, C. L., et al, *Proc Natl Acac Sci* (USA) (1979) 76:3829. Briefly, yeast cultures grown to mid-log phase in YEPD rich medium (yeast extract, peptone and 4% glucose) were washed and protoplasted with zymolyase 5000 (Miles Laboratory) in sorbitol phosphate buffer. Protoplasts were washed, allowed to stand at room temperature for one hour in 67% YEPD containing 1 M sorbitol, then pelleted and suspended in Tris-sorbitol-calcium chloride buffer to $2 \times 10^9$ protoplasts/ml. Protoplasts were mixed with 5-10 $\mu$g of DNA for transformation in a 100 $\mu$l reaction mix, then 1 ml of 44% PEG was added and the mixture allowed to stand for 40 minutes at room temperature.

C.2. Selection for G418 Resistance

For direct G418 resistance selection in yeast, dilutions of the transformation mixture were pipetted onto nutrient agar plates appropriate to the host (YEPD containing 1 M sorbitol and 3% agar) and overlayed with 13 ml of the same nutrient agar (50° C.). After 2-6 hours incubation at 30° C., the plates are overlayed with 4 ml of similar medium (YEPD - 2% agar) and G418. The concentration of G418 for the total volume of agar on the plate (30 ml) was 100 to 250 $\mu$g/ml.

C.3. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 $\mu$g of plasmid or DNA sequence is cleaved by one unit of enzyme in about 20 $\mu$l of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol followed by running over a Sephadex G-50 spin column. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 5-10$\mu$M dNTPs. The Klenow fragment fills in at 5' sticky ends uut chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides are prepared by the triester method of Matteucci, et al, (*J Am Chem Soc* (1981) 103:3185–3191). Kinasing of single strands prior to annealing or for labeling is achieved using an excess, e.g., approximately 10 units of polynucleotide kinase to 1 nmole substrate nn the presence of 50 mM Tris, pH 7.6, 10 mM MgCl$_2$, 5 mM dithiothreitol, 1-2 mM ATP, 1.7 pmoles $\gamma^{32}$ P ATP (2.9 mCi/mmole), 0.1 mM spermidine, 0.1 mM EDTA.

Ligations are performed in 15-30 μl volumes under the following standard conditions and temperatures: 20 mM Tris-Cl pH 7.5, 10 mM MgCl$_2$, 10 mM DTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 μg/ml total DNA concentrations (5-100 nM total end concentration). Intermolecular blunt end ligations (usually employing a 10-30 fold molar excess of linkers) are performed at 1 μM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{+2}$ using about 1 unit of BAP per μg of vector at 60° for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

C.4. Verification of Construction

In the constructions set forth below, correct ligations for plasmid construction are confirmed by transforming *E. coli* strain MM294 obtained from *E. coli* Genetic Stock Center CGSC #6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci* (USA) (1969) 62:1159, following chloramphenicol amplification (Clewell, D. B., *J Bacteriol* (1972) 110:667). The isolated DNA is analyzed by restriction and/or sequenced by the dideoxy method of Sanger, F., et al, *Proc Natl Acad Sci* (USA) (1977) 74:5463 as further described by Messing, et al, *Nucleic Acids Res* (1981) 9:309, or by the method of Maxam, et al, *Methods in Enzymology* (1980) 65:499.

C.5. Hosts

Host strains used in cloning and expression herein are as follows:

For cloning and sequencing, and for expression of construction under control of most bacterial promoters, *E. coli* strain MM294 (supra), Talmadge, K., et al, *Gene* (1980) 12:235; Meselson, M., et al, *Nature* (1968) 217:1110, was used as the host.

Expression in yeast employed a laboratory strain of *S. cerevisiae* designated S173-6B, which is LEU2−, URA3−, TRP1−, HIS4−. This strain is obtainable from Professor Michael Holland, University of California, Davis.

C.6. Verification of DNA Uptake

Transformations using yeast hosts were tested for uptake and replication of the desired sequences by DNA isolation and Southern Blot analysis. DNA is isolated by the method of Sherman, F., et al, *Methods in Yeast Genetics* (1979), Cold Spring Harbor Laboratory. Briefly, after growth to late log phase in the appropriate selective medium (e.g., YEPD and 150 μg/ml G418), cells were washed and protoplasted with zymolyase 5000 (Miles Laboratory) in 1 M sorbitol, 20 mM EDTA. The protoplasts were then pelleted and suspended in 0.15 M NaCl, 0.1 M EDTA, predigested pronase and SDS added and the protoplasts incubated one to three hours at 37° C. The mixture was heated to 70° C. for 15 minutes, put on ice, and potassium acetate added to 0.5M. After 30 minutes on ice, the mixture ws centrifuged and the resulting supernatant treated with RNase and extracted with chloroform and isoamyl alcohol (24:1). The aqueous phase was centrifuged and the resulting supernatant ethanol precipitated, the precipitate was washed and resuspended, and the DNA precipitated with isopropanol.

Southern Blot analysis was done according to the method of Southern, *J Mol Biol* (1975) 98:503. Briefly, the isolated DNA was digested to completion with one or more restriction endonucleases, and run on agarose gels with molecular weight markers. DNA fragments were depurinated, in situ, with 0.075 M HCl, denatured in 0.5 M NaOH, 1.5 M NaCl, and neutralized in 1 M Tris-Cl pH 7.4, 3 M NaCl. The DNA on the gels was transferred to nitrocellulose filters via diffusion blotting in 20 x SSC overnight. The filters were then baked at 80° C. in a vacuum oven for two hours.

Before hybridization with probe, the nitrocellulose filters were prehybidized for 3 hours to overnight at 42° C. in 50% formamide, 5 x SSC, 1/20 P/Pi (P/Pi is 0.05 M sodium pyrophosphate, 0.5 M sodium phosphate, monobasic, 0.5 M sodium phosphate dibasic), 0.1% SDS, 5 x Denhardt's (Denhardt's is 0.02% BSA, 0.02% Ficoll, 0.02% PVP), and 200 μg/ml sheared denatured carrier DNA.

The filters were hybidized with 10$^6$ cpm of (usually) $^{32}$P-labelled, nick-translated DNA probe in a solution of 50% formamide, 5 x SSC, 1/20 P/Pi, 0.1% SDS, 2 x Denhardt's, and 100 μg/ml sheared denatured carrier DNA at 42° C. for 18-24 hours.

The hybridized filters were washed three times in 2 x SSC, 0.1% SDS at room temperature, dried and exposed to x-ray film.

D. DETAILED DESCRIPTION OF PREFERRED EMBODIMENTS

D.1. Construction of Vectors Containing the Modified Truncated Kan Gene Coding Sequences

D.1.a. Construction of pFC19

Figure 2:
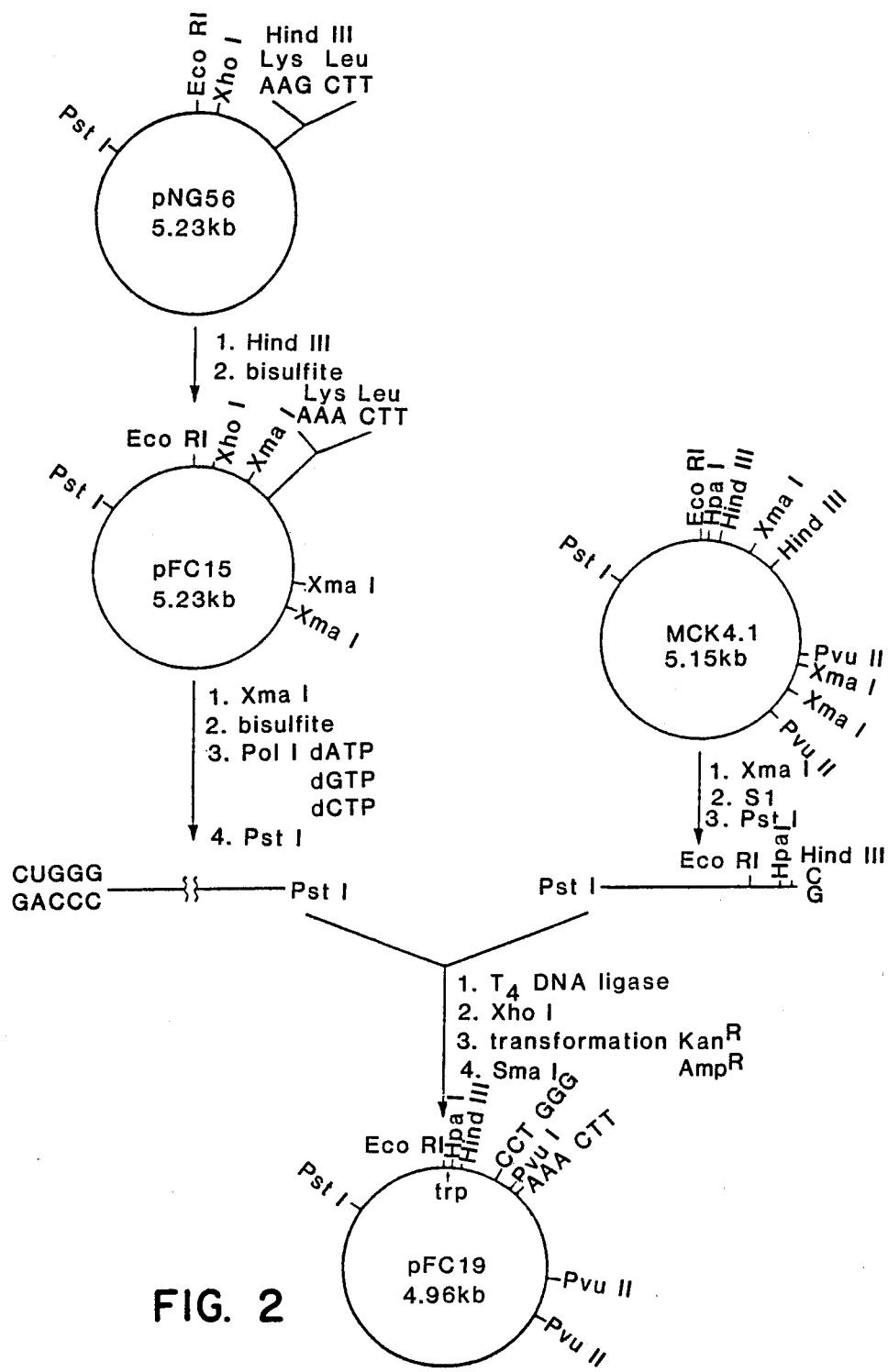
FIG. 2 shows the construction of pFC19.

The construction of pFC19, which contains a modified, truncated form of the DNA sequence encoding G418 resistance by conferring aminoglycoside phosphotransferase activity (mtAPH-I) under trp control, is illustrated in FIG. 2. *E. coli* K12 strain MM294 harboring plasmid pFC19 was deposited with the ATCC on Dec. 22, 1983, and designated ATCC No. 39551.

As shown in FIG. 2, plasmid pFC19 is a ligation product of 5' PstI/blunt-3' DNA fragment containing the trp promoter and the N-terminal ∇2-10 APHI coding sequence from plasmid MCK 4.1 and a mutated, 5'-blunt/PstI-3' DNA fragment from plasmid pFC15 containing a modified C-terminal APH-I sequence. The pFC15 derived fragment in pFC19 contains the majority of the coding sequence for the Kan gene but with a site specific mutation which destroys the HindIII site that is present in the coding sequence, while preserving the wild type amino acid sequence.

Both plasmid MCK4.1 and pFC15 were derived from pNG56, a plasmid containing the entire Kan gene coding sequence. The Kan coding sequence in pNG56 was shown to have a XhoI site at codons 10/11, it can thus be used to furnish the C-terminal codons 11–271 of APH-I by suitable digestion. pFC15 was derived from pNG56 by site specific mutagenesis, and contains a modification at codons 184/185 of the native sequence.

D.1.a.1. Construction of pNG56

Plasmid pNG56 is a derivative of pNG20 (Grindley, N. D. F., et al, *Proc Natl Acac Sci* (USA) (1980) 77:7176). pNG20 encodes only the carboxy-terminal portion and downstream inverted repeat of the 3 kb sequence of APH-I from Tn601 disclosed by Oka, A., et al, *J Mol Biol* (1981) 147:217 (i.e., nucleotides 1701–3094 of the Oka sequences) and thus fails to confer resistance to kanamycin.

pNG56 contains the entire Kan gene coding sequence but lacks, as does pNG20, the approximately 1.04 kb 5' (upstream) inverted repeat present in Tn 601. To obtain pNG56, pNG20 was treated with ClaI (which cuts uniquely upstream of the Tn 601 sequence) and with HindIII (which cuts at codons 184/185 of the coding sequence). The desired control and N-terminal coding sequences were added by isolating the appropriate fragments resulting from TaqI/XhoI and XhoI/HindIII digestion of pNG23, (Grindley, N. D. F., et al, (supra)) and performing a 3-way ligation of these two fragments with vector (ClaI and TaqI sticky ends are compatible). The ligation mixture was transformed into MM294 selecting for $Amp^R$, $Kan^R$ and correct construction confirmed using standard methods.

D.1.a.2. Construction of pFC15 pNG56 was linearized with hindIII, and mutated with sodium bisulfite using the procedure of Shortle, D., et al, *Proc Natl Acad Sci* (USA) (1978) 75:2170. After removal of the bisulfite, the mutagenized DNA was ligated (redigested with HindIII), and used to transform *E. coli* K12 strain MM294. $Kan^R$ transformants were screened for plasmids which had lost a HindIII recognition site, and the successful plasmid constructions re-transformed into *E. coli* MM294 for purification. $Kan^R$ transformants were agin selected. The correct construction was verified by restriction enzyme analysis and sequencing. Codons 184/185 were verified to have been changed from
AAG CTT to AAA CTT
Lys Leu Lys Leu

D.1.a.3. Construction of MCK 4.1

MCK 4.1 which was used to provide the trp promoter sequence and the truncated front end of the Kan gene was constructed from pNG56 and pDG141 as shown in FIG. 1 as follows:
- pNG56 was digested to completion with XhoI, repaired with PolI Klenow fragment in the presence of all four dNTPs, and digested with EcoRI. The large approximately 5 kb fragment was isolated. It contains the coding sequence for all but the first ten codons of APH-I, blunt ended so as to be in 0 reading frame with an upstream sequence.
- pDG141 harbors the trp promoter operably linked to an ATG start codon, followed by a SacI site. It was deposited with the ATCC Jan. 24, 1984, and has accession number 39588. pDG141 was digested with SacI, treated with PolI as above, and digested with EcoRI. The small 116 bp promoter/ribosome binding site and ATG start codon fragment, which is blunt ended so as to be in 0 reading frame with downstream sequence, was purified by acrylamide gel electrophoresis and electroelution.

The pNG56 vector fragment and the promoter containing pDG141-derived fragment were ligated at about 200 µg/ml (1:1 molar ratio) under "sticky end" conditions, diluted fourfold, and the DNA fragments ligated under blunt-end conditions. The ligation mixture was used to transform *E. coli* MM294 and transformants selected for $Amp^R$ (50 µg/ml) and screened with increasing concentrations of kanamycin (5, 10, and 15 µg/ml). Plasmid DNA was isolated from $Amp^R$ and $Kan^R$ (more than 10 µg/ml) candidates and analyzed by restriction enzyme digestion and DMA sequence analysis. A successful construction, which was designated MCK4.1, yielded a unique HpaI DNA fragment, a 530 bp HindIII DNA fragment, and the expected altered RsaI digestion pattern.

Figure 3:
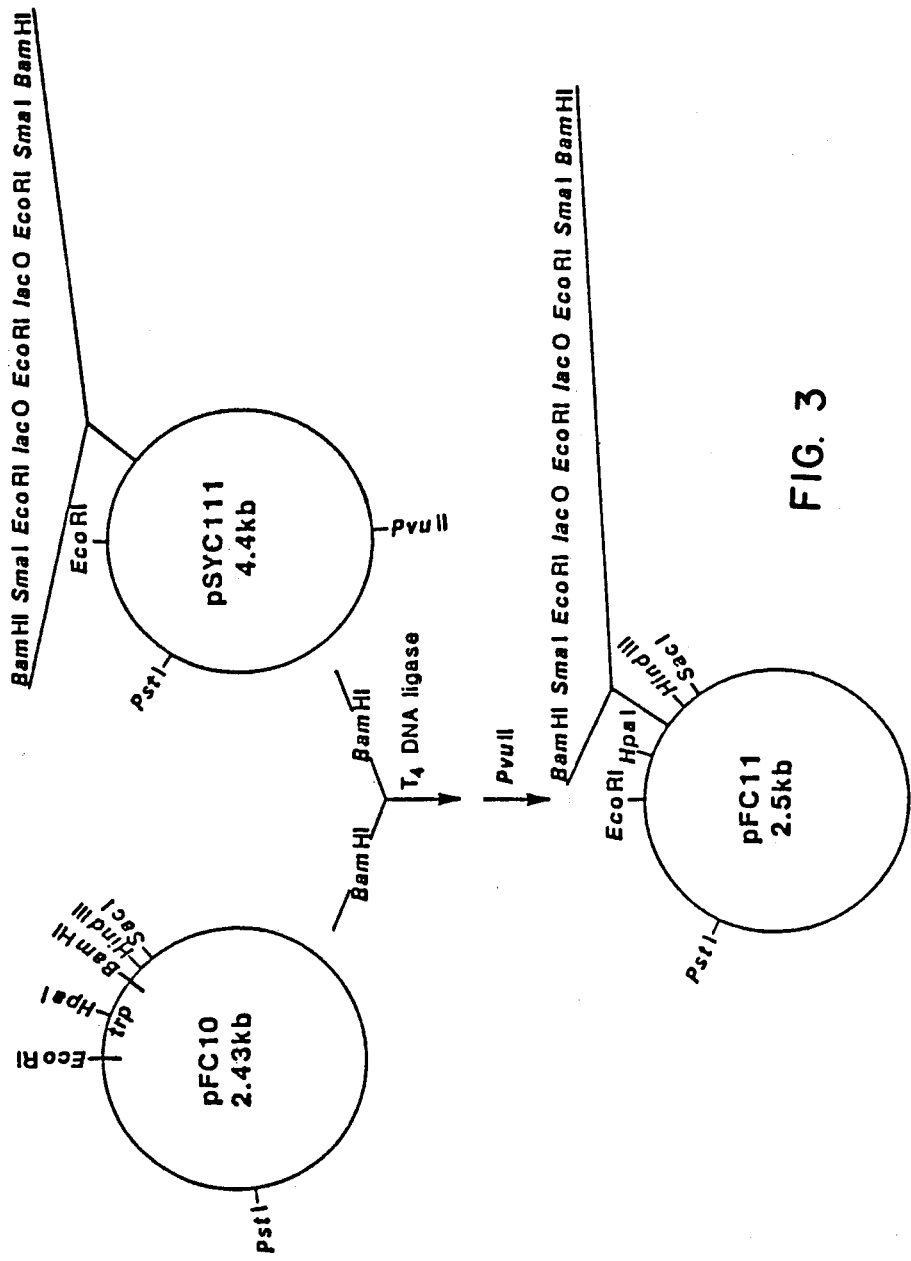
FIG. 3 shows the 5' terminal coding sequences for the Kan gene in pNG56 and in pMCK4.1 along with the corresponding N-terminal amino acid sequences and the levels of Kan resistance conferred on *E. coli* MM294 by transformation with these vectors.

Sequences of the regions surrounding the ATG start codon of PNG56 and pMCK4.1 are shown in FIG. 3.

D.1.a.4. Completion of pFC19 pFC15 was then itself mutagenized using the same technique following digestion with XmaI. The XmaI digested, mutagenized frragments from pFC15 were repaired with *E. coli* DNA polymerase I (PolI), Klenow fragment, in the presence of dCTP, dGTP, dATP and then the flush ended DNA fragments disgested with PstI and concentrated.

To prepare the MCK4.1 fragment, pMCK4.1 was digested with XmaI, treated with S1 nuclease under mild conditions (1 µl S1/150 µl reaction at 20° C., 20 min), and the fragments treated with PstI and concentrated.

The pFC15 and MCK 4.1 fragments were ligated at a 1:1 molar ratio of 0.62 µmolar ends for 5 hrs at 4° C. using 40 µM ATP and then overnight at 14° C. using 1 mM ATP. The ligation mixture was digested with XhoI to inactivate the Kan promoter fragment of PFC15and used to transform MM294. Colonies were selected in liquid medium containing ampicillin (50 µg/ml). THe $Amp^R$ enriched transformed population was diluted and grown in medium containing Amp (50 µg/ml) and Kan (20 µg/ml) and plasmid DNA purified from $Amp^R$ $Kan^R$ transformants. The plasmid preparation was digested with SmaI to eliminate non-mutants and retransformed into *E. coli* strain MM294. Plasmid DNA was isolated from $Kan^R$ $Amp^R$ colonies and the correct construction confirmed by restriction analysis and DNA sequencing. The desired construct was designated pFC19. In pFC19, the XmaI/SmaI site at codons 93/94 of the ∇2–10 tAPH-I sequence had been mutagenized so that codons 93/94 were altered from
CCC GGG to CCT GGG
Pro Gly Pro Gly.

D.1.b. Construction of pDG144 and pFC20 pDG144 contains the coding sequence for the modified trunctated Kan gene ∇2–10, immediately preceded by a linker fragment containing EcoRI, SmaI, BamHI, and HindIII restriction sites; in pFC20, this linker is also preceded by a duplicated lac operator, an inverted repeat of this linker, and the trp promoter. Both contain, distal to the 3' translation termination codon, convenient StuI (in dcm- *E. coli* hosts), HaeII, MluI, BssHII, MstI and PvuII sites. pDG144 was constructed from pFC19 in several steps through pFC20 as an intermediate (see FIG. 4). pDG144 was deposited with the ATCC on Jan. 13, 1984, ATCC No. 39579.

Figure 4:
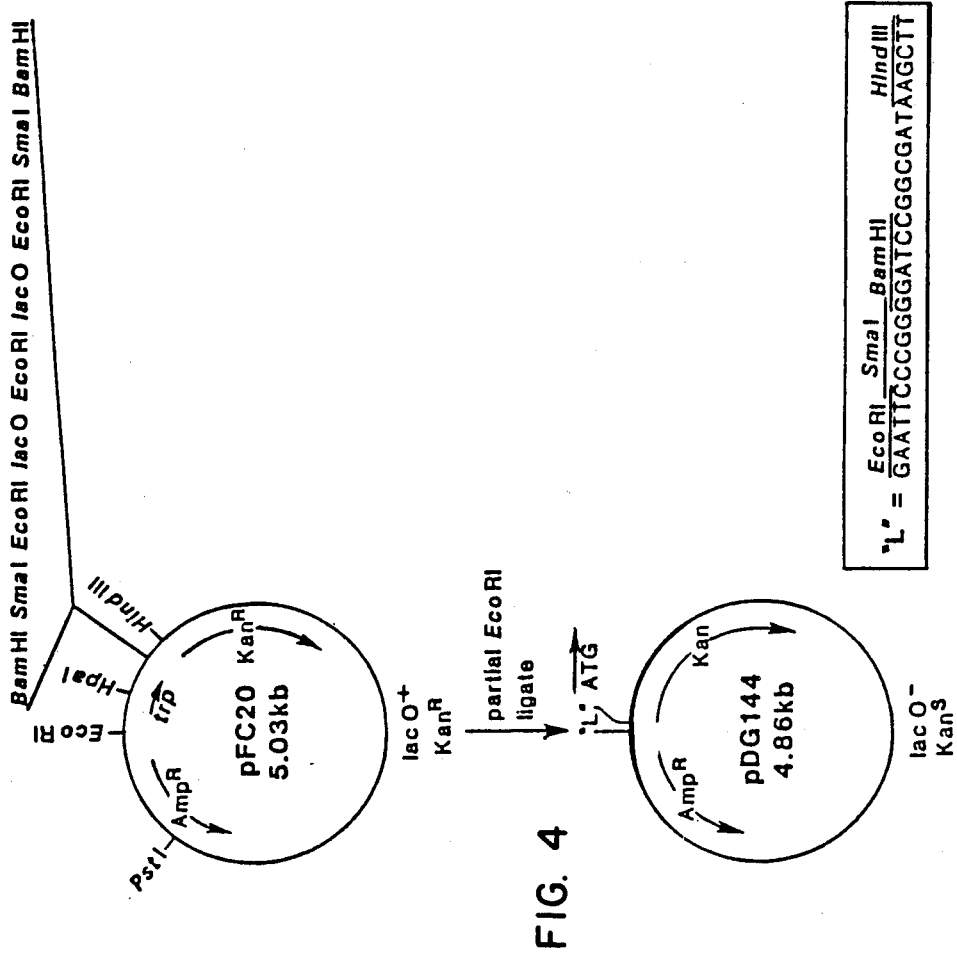
FIG. 4 shows the construction of pFC11.

D.1.b.1. Construction of pFC20 pFC19 was first digested with HpaI to inactivate the trp promoter, and then with PstI and HindIII. pFC11 (see below) was digested with PstI and HindIII to liberate the trp promoter and desired lac operator/linker fragment. These fragments were ligated under sticky-end conditions (3:1 molar ratio). The ligated DNA was digested with SacI to inactivate unwanted ligation products, and the mixture used to transform E. coli MM294. Successful transformants were selected for Amp$^R$, LacO+ and Kan$^R$, and plasmid DNA isolated. The correct construction of pFC20 was confirmed by restriction analysis. pFC20, as shown in FIG. 5, contains the desired linker/lac operator preceding the mtAPH-I 5' HindIII site, which is downstream from the trp promoter.

pFC11, used as the source of the polylinker/lacO sequences in pFC20, and ultimately as a source of the polylinker in pDG144, was constructed from pDG141 (supra) in two steps, the second of which is shown in FIG. 4:

pDG141 was first modified to convert a ClaI site at the 3' end of the trp promoter to a BamHI site by the conventional procedure, i.e., treatment of pDG141 with ClaI, blunt ending with Klenow, and blunt-end ligation with a commercial BamHI linker. The resulting ligation mixlture was used to transform MM294 to Amp$^R$ and the presence of a BamHI site verified in the desired pFC10. pFC10 (FIG. 4) was digested with BamHI and ligated with BamHI digested pSYC111, (a 4.4 kb vector which had, in turn, been prepared by insertion of the desired 72 bp fragment into the BamHI site of pBR322; [This 72 bp fragment has the sequence: BamHI, SmaI, EcoRI, lacO, EcoRI, lacO, EcoRI, SmaI, BamHI]). The ligation mixture was digested with PvuII and used to transform MM294 to Amp$^R$, LacO+ and screened for Tet$^S$. The correct construction of pFC11 was confirmed by restriction enzyme analysis.

D.1.b.2. Completion of pDG144

To obtain pDG144, pFC20 was treated as shown in FIG. 5. The trp promoter and lac operators were removed from pFC20 by digesting to completion with EcoRI, religating, and transforming MM294 to lacO$^-$ Kan$^S$. The correct construction, pDG144, contains the 22 bp polylinker bearing EcoRI, SmaI, and BamHI sites immediately upstream of the 5' HindIII site of mtAPH-I.

Digestion of pDG144 with HindIII and, respectively, StuI (when cloned in dcm-hosts) HaeII, MstI or PvuII yields DNA fragments containing the entire coding sequence of the ∇2–10 Kan gene of 1.03, 1.08, 1.15, or 1.21kb. In these fragments, the ATG start codon is proximal to the 5' HindIII end.

D.2. Vectors and Derivatives with Mammalian Control Sequences

Figure 6:
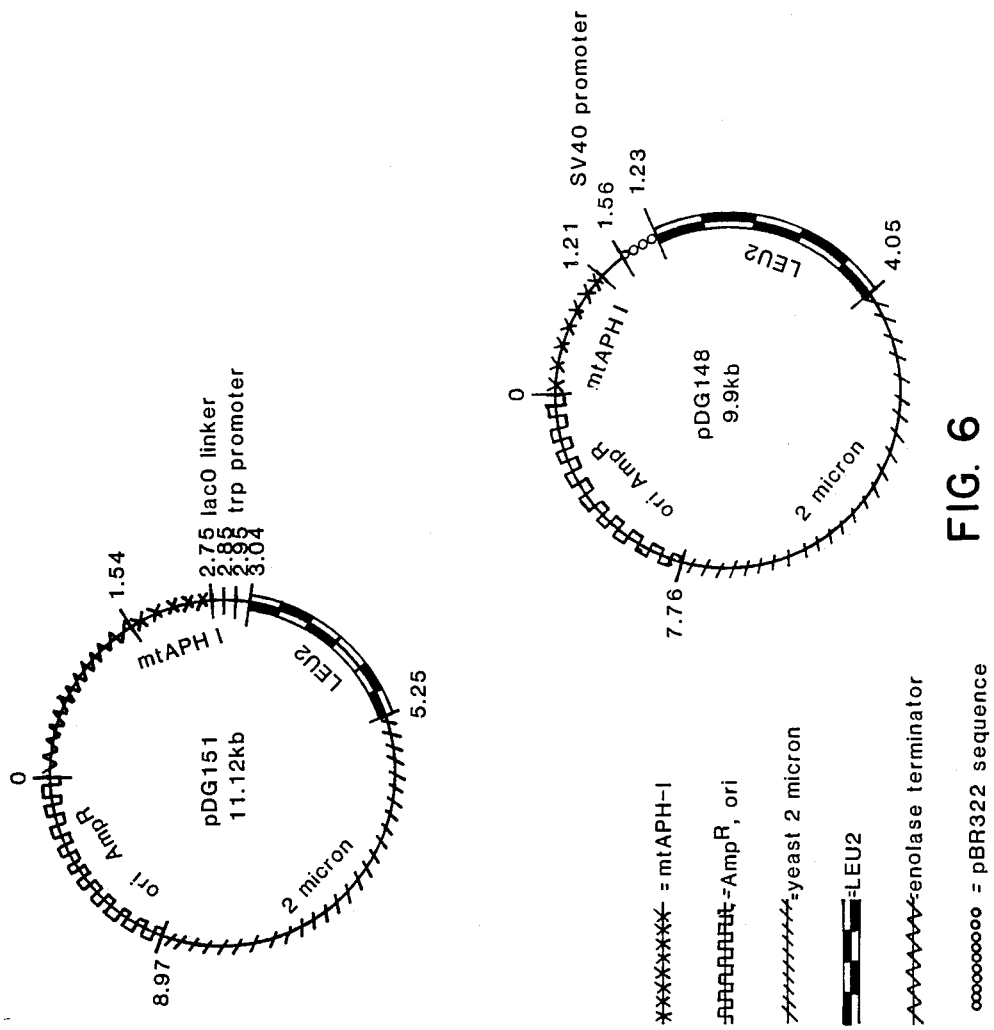
FIG. 6 shows schematically the features of pDG148 and pDG151.

D.2.a. pDG148 (SV40 Control)

pDG148, diagrammed in FIG. 6, contains the truncated ∇2–10 Kan gene under control of the SV40 promoter. pDG148 will replicate autonomously both in procaryotic (e.g., E. coli) and in eucaryotic (e.g., yeast and certain mammalian cell line) hosts. pDG148 was deposited with ATCC on Dec. 22, 1983, and was given accession number 20695. The sequences in pDG148 (with reference to FIG. 6) are as follows:

1. The 1.21kb fragment comprising the first 1.21 kb of pDG148 is the HindIII/PvuII modified truncated Kan gene cassette from pDG144. This sequence, as stated above, has been mutated at codons 93/94 (of the truncated gene) to eliminate the XmaI/SmaI recognition site and at codons 175/176 to destroy the HindIII recognition site while retaining the same amino acid sequence in the encoded protein.
2. The SV40 viral promoter sequence containing the SV40 origin of replication, early viral promoter and transcriptional enhancer, is obtained by digesting isolated SV40 DNA with HindIII and PvuII and ligating the blunt-ended PvuII end to a BamHI linker obtained from New England Biolabs. This occupies coordinates 1.21–1.56.
3. Coordinates 1.56 kb to 1.83 kb are a 276 bp DNA fragment from pBR322 obtained by double digestion with BamHI and SalI and isolation of the 276 bp fragment.
4. The LEU2 gene from yeast occupies coordinates 1.83 kb-4.05 kb. This is derived from YEp13 (Broach, J., et al, Gene (1979) 8:121) by double digestion of this plasmid with XhoI/SalI.
5. A yeast replication origin derived from the yeast 2 micron plasmid occupies coordinates 4.05 kb-7.76 kb. It is obtained by digestion of pDB248 (Beach, D., et al, Nature (1981) 290:140) with EcoRI(repair)/SalI and isolation of the 3.7 kb DNA fragment containing the replicon. The existence of the appropriate SalI site was not deducible from the disclosure of Beach. However, pDB248 was shown to contain a SalI site about 50 ,bp downstream from the indicated LEU2 region/2μ PstI tailing site as set forth in the Beach reference.
6. Finally, this plasmid is capable of replication in E. coli and of conferring Amp resistance by inclusion of a 2145 bp DNA fragment obtained from Br322 by double digestion with TthIIII(repair) and EcoRI. It occupies coordinates 7.76kb-9.9 kb of the 9.9 kb pDG148.

D.2.b. Construction of pDG151 pDG151 deposited with ATCC May 11, 1984 and given accession number 39686, is a 11.12 kb plasmid analogous to pDG148, except that the modified truncated Kan gene is linked to additional procaryotic control systems comprising duplicated lac operators in front of a trp promoter and is preceded by a polylinker. The eucaryotic promoter sequences linked to mtAPH-I have been deleted, and the vector contains, downstream from the trp promoter a 0.1 kb sequence containing a duplicated lac operator flanked by a short inverted repeat polylinker. Expression of the mtAPH-I can thus be regulated by either tryptophan levels or lac repressor synthesis. This fragment was derived by HindIII/BamHI(partial) digestion of pFC20 (see § D.1.b.1).

The sequences of pDG151 are outlined in FIG. 6, and consist of the following:

1. Coordinates 0–1.54 are the 1.54 kb HindIII/EcoRI 3' untranslated terminator sequences of the EnoI gene derived from peno46 (Holland, M. J., et al, J Biol Chem (1981) 256:1385). The resulting EcoRI site is at coordinate 0, and the blunt end is ligated to the mtAPH-I sequence 2. Coordinates 1.54–2.75 contain the truncated Kan gene modified as noted above. This is the same HindIII/PvuII digest of pDG144 which corresponds to the sequence occupied by coordinates 0–1.21 in pDG148.
3. Coordinates 2.75–2.85 contain the duplicated lac operator sequence flanked by inverted polylinker repeats and was obtained from pFC20 (see FIG. 4) by digestion with HindIII and BamHI(partial). Correct BamHI digestion to give the fragment which includes the lacO duplication was readily verifiable by transforming hosts to Amp$^R$ and then screening for constituitive LacZ+ expression in *E. coli* K12 strain MM294. The sequence immediately preceding the ATG start codon (at 2.75) is:

```
5'G AAT TCC CGG GGA TCC GGC GAT AAG CTT ATG
   EcoRI  XmaI    BamHI         HindIII
```

4. Coordinates 2.85–2.95 are the isolated 107 bp 5'-EcoRI(repaired)/BamHI-3' fragment from pFC10. This fragment contains the trp promoter-operator and is analogous to the 112 bp trp control fragment which occupies coordinates 5.80–5.91 kb in pDG149.
5. Coordinates 2.95–3.04 kb contain a 90 bp pBR322 segment between the SphI(repair) and SalI sites.
6. The LEU2 gene from yeast occupies coordinates 3.04–5.25. It was obtained as an XhoI/SalI digest fragment from YEp13 and is the same fragment as that which occupies a similar location in pDG148.
7. The 2 micron plasmid replicon in coordinates 5.25–8.97 is analogous to the pDB248 derived fragment in pDG148.
8. Coordinates 8.97–11.12 contain a TthlllI(repair)-/EcoRI digest of pBR322 which supplies Amp$^R$ and an *E. coli* origin of replication.

As pDG151 contains a polylinker preceding the ATG start of mtAPH-I, convenient restriction sites for creation of 5' fusion termini are available.

D.2.c. Construction of pDG151::RSV pDG151::RSV is a *S. cerevisiae/E. coli* shuttle vector using control sequences derived from Rous Sarcoma Virus. It is constructed from pDG151 by removing the sequences between coordinates 3.04 and 2.75 and replacing them with the RSV promoter sequences (religation at the ATG-preceding HindIII site regenerates operable linkage of the promoter with the mtAPH-I codons).

Plasmid pDG151 was digested to completion with SalI, treated with *E. coli* DNA polymerase I, Klenow fragment, in the presence of all four dNTPs, and finally digested to completion with HindIII. Plasmid pRSV-NeoI (see below) was digested to completion with NruI and HindIII. The digested DNA fragments were mixed (1:2.5 molar ratio) and ligated at 50 μg/ml (total DNA concentration) under sticky-end conditions. The ligated linear DNA fragments were diluted to 25 μg/ml and further ligated under blunt-end conditions to favor intramolecular circle formation. The ligated DNA was digested with PvuII (to inactivate undesired pRSV-NeoI ligation products) and 150 ng of the DNA used to transform *E. coli* K12 strain MM294 to ampicillin resistance. Non-constitutive Lac+ colonies (absence of 280 bp SalI/HindIII DNA fragment of pDG151) were screened for kanamycin resistance. Amp$^R$Kan$^R$ candidate colonies were screened for the presence of the desired 11.24 kb plasmid containing the 400 bp NruI/HindIII DNA fragment encoding the Rous Sarcoma virus promoter. Plasmid pDG151::RSV (11.24 kb) released the diagnostic 1235 bp EcoRI fragment (fusion of 928 bp of LEU2 DNA to 307 bp of RSV DNA), regenerated the desired SalI recognition site (SalI repair, GTCGA/CGA, NruI fusion) and generated the diagnostic SalI/EcoRI (307 bp) and NruI/EcoRI (150 bp) DNA fragments.

D.2.c.1. Construction of pRSVNeoI

Plasmid pRSVneo (5.73 kb, renamed here pRSVneoII to distinguish the APH-II coding sequence from the modified, truncated APH-I coding sequence of this invention) as been described (Gorman, C., et al, Science (1983) 221:551–553). pRSVneoII was modified to give pRSVNeoI by substituting the 1210 bp HindIII/PvuII DNA fragment encoding the mtAPH-I coding sequence (from plasmid pFC20) for the 1352 bp HindIII/PvuII region of pRSVneoII encoding the bacterial promoter and structural coding sequences for APH-II (Beck, E., et al, Gene (1982) 19:327).

Plasmid pRSVneoII was digested to completion with PvuII and HindIII. Plasmid pFC20 was digested to completion wth PvuII and HindIII. The digested DNA fragments were mixed (1:1 molar ratio) and ligated at 40 μg/ml (total DNA concentration) under sticky-end conditions. The ligated linear DNA fragments were diluted to 20 μg/ml and further ligated under blunt-end conditions to favor intramolecular circle formation. *E. coli* K12 strain MM294 was transformed to Amp$^R$ with 150 ng of the ligated DNA and non-constitutive Lac+ colonies (transformed with the pRSVneoII origin containing fragment rather than the pFC20 origin containing fragment) were screened for the presence of the desired 5.59 kb plasmid. Plasmid candidates were screened with HindIII (unique site), PvuII (unique site), HindIII/PvuII (4.3 and 1.21 kb DNA fragments), and EcoRI (3.04 and 2.55 kb DNA fragments). Plasmid DNA from one transformant, designated pRSVneoI (5.59 kb), encoded the mtAPH-I coding sequence substituted for the APH-II promoter and coding sequence. Additionally, plasmid pRSVneoI conferred a high level of kanamycin resistance to *E. coli* K12 strain MM294 (>100 μg/ml).

E. Expression Under Mammalian Promoter Control in Yeast

The ability of promoters normally operable in mammalian cells to effect expression in yeasts is shown by the results in Table 1. (pDG150 and pLK11.17 contain the coding sequences in operable linkage to native yeast promoters.)

TABLE 1

| Plasmid | Promoter | Transformation Frequency 100 μg G418/ml | 200 μg G418/ml |
|---------|----------|------------------------------------------|-----------------|
| pDG150 | ENO1 | $1.2 \times 10^3$ | $0.18 \times 10^3$ |
| pLK11.17 | LEU2 | $1.3 \times 10^3$ | $0.98 \times 10^3$ |
| pDG148 | SV40 early | $0.5 \times 10^3$ | $0.12 \times 10^3$ |
| pDG151::RSV | Rous LTR | $1.2 \times 10^3$ | $0.83 \times 10^3$ |

Plasmids encoding mtAPH operably linked to control sequences appropriate to eucaryotes were used to transform *S. Cerevisiae* S173-6B protoplasts as described. As shown in Table 1 transformation frequencies of the expected magnitude, were obtained. Frequencies, expressed as directly selected G418$^R$ transformants/μg of plasmid DNA, are comparable whether mammalian or yeast promoters are used.

Figure 7:
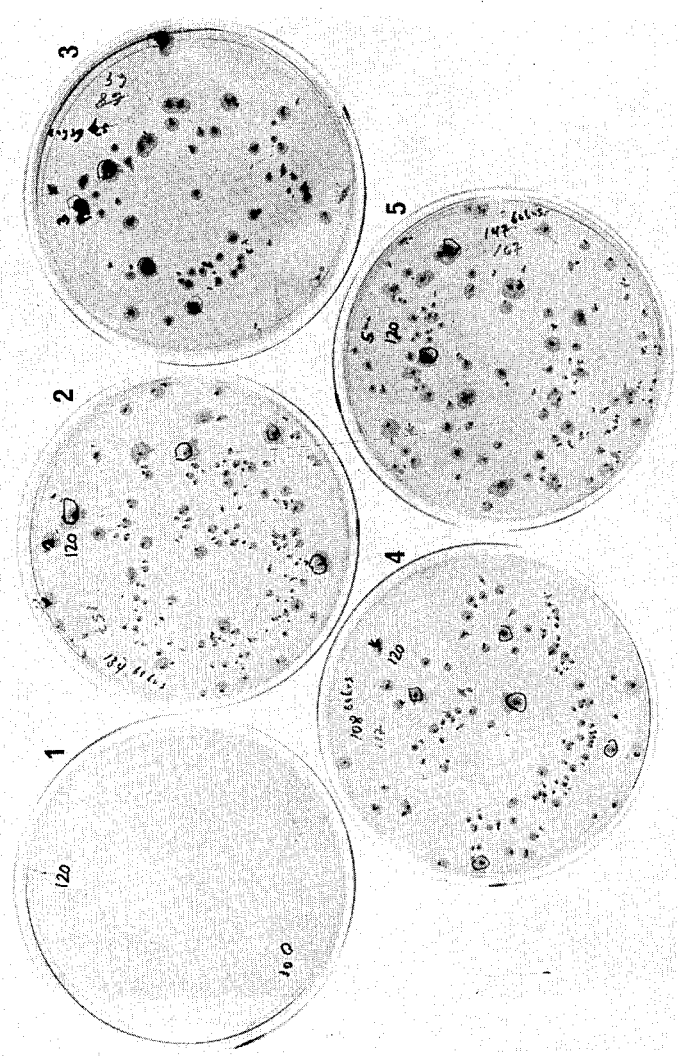
FIG. 7 shows the results of G418 direct selection of a laboratory yeast strain transformed with vectors of the invention.

The results of Table I are also shown in FIG. 7 which compares selection (growth) on G418 containing medium of both transformed and non-transformed S173-6B: (1) no plasmid; (2) pLK11.17; (3) pDG148; (4) pDG150; (5) pDG151::RSV.

The transformation frequencies selected by G418 were 2–4 fold higher than those obtained using LEU2+selection.

Southern blots of DNA extracted from transformed yeast performed according to the procedure of §C.6, further confirmed the presence of the mtAPH-I coding sequence in the transformed hosts.

The level of G418 resistance conferred on yeast by plasmids containing mammalian control systems is functionally useful for direct selection. Controls were conducted using no plasmid, and using the yeast promoter containing plasmids pDG150 and pLK11.17. Table 2 shows the concentrations of antibiotic required to give a 50% plating efficiency for plasmid-containing *S. cerevisiae* strain S173-6B.

TABLE 2

| Plasmid | G418 Concentration |
| --- | --- |
| None | <25 μg/ml |
| pDG148 | 160 μg/ml |
| pDG150 | >1000 μg/ml |
| pDG151::RSV | 500 μg/ml |
| pLK11.17 | >1000 μg/ml |

Transformation of *E. coli* with pDG151::RSV (or pRSVneoI) also resulted in cultures having kanamycin resistance at roughly the same level as that given using a bacterial promoter, thus showing the trifunctionality of the RSV promoter.

The following plasmids have been deposited at the American Type Culture Collection, Rockville, Md., U.S.A. (ATCC) under the terms of the Budapest Treaty on the International Recognition of the Deposit of Microorganisms for the Purposes of Patent Procedure and Regulations thereunder (Budapest Treaty) and are thus maintained and made available according to the terms of the Budapest Treaty. Availability of such strains is not to be construed as a license to practice the invention in contravention of the rights granted under the authority of any government in accordance with its patent laws.

The deposited plasmids have been assigned the indicated ATCC deposit numbers. The plasmids have also been deposited with the Master Culture Collection (CMCC) of Cetus Corporation, Emeryville, Calif., U.S.A., the assignee of the present application, and assigned the indicated CMCC deposit numbers:

| Plasmid | CMCC Deposit No. | ATCC No. | ATCC Deposit Date |
| --- | --- | --- | --- |
| pFC19 | 1832 | 39551 | Dec. 22, 1983 |
| pDG141 | 1966 | 39588 | Jan. 24, 1984 |
| pDG144 | 1960 | 39579 | Jan. 13, 1984 |
| pDG148 | 1929 | 20695 | Dec. 22, 1983 |
| pDG151 | 1828 | 39686 | May 11, 1984 |

We claim:

1. A method for producing a desired peptide in Saccharomyces yeast, which method comprises culturing Sacchoromyces yeast cells transformed with an expression vector comprising the DNA sequence encoding the peptide operably linked to a promoter selected from the group consisting of the Sv40 early promoter and the RSV promoter.

2. A recombinant Saccharomyces yeast host cell transformed with a recombinant vector effective in expressing, in said yeast, a DNA sequence encoding a desired peptide, which vector comprises said DNA sequence operably linked to a promoter selected from the group consisting of the SV40 early promoter and the RSV promoter.

3. The yeast cell of claim 2 wherein the vector further includes termination sequences normally operable in eucaryotic cells.

4. The yeast cell of claim 2 wherein said vector, the DNA sequence encoding the desired protein encodes a dominant selectable marker operable in wild-type Saccharomyces yeast.

5. The yeast cell of claim 2 wherein the vector further includes a second DNA sequence encoding a dominant selectable maker operable in wild-type Saccharomyces yeast.

6. A recombinant vector effective in expressing in Saccharomyces yeast cells the DNA sequence encoding a desired peptide, which vector comprises said DNA sequence operably linked to a promoter selected from the RSV promoter and SV40 promoter, and wherein said vector further includes both an origin of replication and a selectable marker, both operable in said yeast.

7. Recombinant host Saccharomyces yeast cells transformed with the vector of claim 6.

8. A method for expressing a desired polypeptide in a host cell selected from group onsisting of prokaryotic and Saccharomyces host cells, which method comprises transforming said prokaryotic or Saccharomyces host cell with an expression vector, which vector comprises; the RSV promotor operably linked to a DNA sequence coding for said desired polypeptide, a Saccharomyces origin of replication, a selectable marker which is expressed in Saccharomyces, a prokaryotic origin of replication, and a selectable marker which is expressed in said prokaryote; and culturing said Saccharomyces or prokaryotic host cell under conditions that permit expression of the desired polypeptide.

* * * * *

UNITED STATES PATENT AND TRADEMARK OFFICE
CERTIFICATE OF CORRECTION

PATENT NO. : 4,870,013  Page 1 of 4

DATED : September 26, 1989

INVENTOR(S) : David H. Gelfand et al.

It is certified that error appears in the above-identified patent and that said Letters Patent is hereby corrected as shown below:

ON THE TITLE PAGE

Item [56], column 1, line 30, change "*Succharomyces Cerevisiae*" to --*Saccharomyces cerevisiae*--.

Item [56], colulmn 2, line 5, change "*Succharomyces Cerevisiae*" to --*Saccharomyces cerevisiae*--.

Item [56], line 13, change "Saccharomyces Cerevisiae" to --*Saccharomyces cerevisiae*--.
Item [56], line 22, "Saccharomyces Cerevisiae" to --Saccharomyces cerevisiae--.
Item [56], line 25, "Pambe" to --Pombe--.

Column 1, line 49, change "cdding" to --coding--.

Column 2, line 56, change "provide" to --provides--.

Column 3, line 51, delete the "period" after polyadenylation.

Column 4, line 62, change "sequences" to --sequence--.

Column 4, line 64, after "such" insert --a--, and change "sequences" to --sequence--.

Column 5, line 55, change "*Acac*" to --*Acad*--.

Column 5, line 65, delete the hard space return.

Column 6, line 50, change "uut" to --but--.

Column 6, line 65, change "nn" to --in--.

UNITED STATES PATENT AND TRADEMARK OFFICE
CERTIFICATE OF CORRECTION

PATENT NO. : 4,870,013
DATED : September 26, 1989
INVENTOR(S) : David H. Gelfand et al.

It is certified that error appears in the above-identified patent and that said Letters Patent is hereby corrected as shown below:

Column 8, line 8, change "hoursaat" to --hours at--.

Column 8, line 10, change "ws" to --was--.

Column 8, line 29, change "prehybidized" to --prehybridized--.

Column 8, line 36, change "hybidized" to --hybridized--.

Column 8, line 37, change "32p-labelled" to --$^{32}$P-labelled--.

Column 9, line 36, change "hindIII" to --HindIII--.

Column 9, line 45, change "agin" to --again--.

Column 9, lines 49 and 50 align "Lys" directly under "AAG", align "Leu" directly under "CTT", align "Lys" directly under "AAA" and align "Leu" directly under "CTT".

Column 10, line 16, change "DMA" to --DNA--.

Column 10, line 22, change "PNG56" to --pNG56--.

Column 10, line 27, change "frragments" to --fragments--.

Column 10, line 30, change "disgested" to --digested--.

Column 10, line 38, change "of" to --at--.

UNITED STATES PATENT AND TRADEMARK OFFICE
CERTIFICATE OF CORRECTION

PATENT NO. : 4,870,013  Page 3 of 4
DATED : September 26, 1989
INVENTOR(S) : David H. Gelfand et al.

It is certified that error appears in the above-identified patent and that said Letters Patent is hereby corrected as shown below:

Column 10, line 41, change "PFC15" to --pFC15-- and add a space after "pFC15".

Column 10, line 43, change "THe" to --The--.

Column 10, lines 56 and 57 align "Pro" directly under "CCC", align "Gly" directly under "GGG", align "Pro" directly under "CCT" and align "Gly" directly under "GGG".

Column 11, line 31, change "mixlture" to --mixture--.

Column 12, line 30, delete the "hyphen" after "EcoRI(".

Column 12, line 35, change "50, bp" to --50 bp--.

Column 12, line 40, change "Br322" to --pBR322--.

Column 12, line 68, after "sequence" insert a --period--.

Column 14, line 25, change "wth" to --with--.

Column 14, line 66, change "*Cerevisiae* to --*cerevisiae*--.

Column 16, in Claim 1, line 13, change "Sacchoromyces" to --Saccharomyces--.

Column 16, in Claim 1, line 16, change "Sv40" to --SV40--.

UNITED STATES PATENT AND TRADEMARK OFFICE
CERTIFICATE OF CORRECTION

PATENT NO. : 4,870,013

DATED : September 26, 1989

INVENTOR(S) : David H. Gelfand et al.

It is certified that error appears in the above-identified patent and that said Letters Patent is hereby corrected as shown below:

Column 16, in Claim 8, line 46, change "from group onsisting" to --from a group consisting--.

Signed and Sealed this

Ninth Day of April, 1991

*Attest:*

HARRY F. MANBECK, JR.

*Attesting Officer*     *Commissioner of Patents and Trademarks*